(12) United States Patent
Chow et al.

(10) Patent No.: US 7,670,554 B2
(45) Date of Patent: Mar. 2, 2010

(54) AUTOMATED ANALYZER

(75) Inventors: Allan Tit-Shing Chow, Wilmington, DE (US); William Jackson Devlin, Sr., Lincoln University, PA (US); Timothy Patrick Evers, Wilmington, DE (US); David Russell Thompson, Kennett Square, PA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 718 days.

(21) Appl. No.: 11/261,952

(22) Filed: Oct. 27, 2005

(65) Prior Publication Data

US 2006/0051243 A1 Mar. 9, 2006

Related U.S. Application Data

(63) Continuation of application No. 10/862,507, filed on Jun. 7, 2004, now Pat. No. 7,381,370.

(60) Provisional application No. 60/488,336, filed on Jul. 18, 2003.

(51) Int. Cl.
*G01N 21/00* (2006.01)

(52) U.S. Cl. ............... 422/64; 422/63; 422/82.03; 436/172; 436/50

(58) Field of Classification Search ... 422/82.05–82.08, 422/63, 64, 68.1, 82.03; 436/50, 172
See application file for complete search history.

(56) References Cited

U.S. PATENT DOCUMENTS 4,325,910 A * 4/1982 Jordan .................... 422/64
4,366,118 A 12/1982 Bunce et al.
4,431,924 A 2/1984 Suovaniemi et al. ........ 250/566
4,517,160 A 5/1985 Galle et al.
4,690,900 A 9/1987 Kimmo et al. ............. 436/47
4,774,055 A 9/1988 Wakataka et al. .......... 422/64
5,202,091 A 4/1993 Lisenbee ................... 422/64
5,340,716 A 8/1994 Ullman et al.
5,482,861 A * 1/1996 Clark et al. ................ 436/48
5,496,519 A 3/1996 Schaqcher ................. 422/64
5,693,292 A 12/1997 Choperena et al. ......... 436/47
5,837,195 A * 11/1998 Malek et al. ............... 422/52
5,968,731 A 10/1999 Layne et al. ............... 422/64
6,042,785 A 3/2000 Harju
6,057,163 A 5/2000 McMillan
6,063,340 A 5/2000 Lewis et al. ............... 422/102
6,074,615 A 6/2000 Lewis et al. ............... 422/102
6,086,824 A 7/2000 Fanning et al. ............ 422/64
6,097,025 A 8/2000 Modlin et al.

(Continued)

FOREIGN PATENT DOCUMENTS

JP H08-54399 A 2/1996

(Continued)

*Primary Examiner*—Robert J Hill, Jr.
*Assistant Examiner*—Cedric Chan
(74) *Attorney, Agent, or Firm*—Leland K. Jordan

(57) ABSTRACT

An automated analyzer for analyzing patient samples. The analyzer includes a plurality of cuvettes, which allow the samples to be mixed with various reagents. The analyzer includes one or more detectors, including a detector adapted to detect luminescence of the reaction mixture in the cuvettes. The analyzer allows for various diagnostic assays to be performed on a single system, and provides for high-sensitivity analysis at faster speeds.

3 Claims, 14 Drawing Sheets

U.S. PATENT DOCUMENTS

| | | | |
|---|---|---|---|
| 6,375,898 B1 | 4/2002 | Ulrich | 422/64 |
| 6,436,349 B1 | 8/2002 | Carey et al. | 422/64 |
| 6,461,570 B2 | 10/2002 | Ishihara et al. | 436/47 |
| 6,498,037 B1 | 12/2002 | Carey et al. | 436/50 |
| 6,555,062 B1 | 4/2003 | Lewis et al. | 422/63 |
| 6,592,818 B2 | 7/2003 | Ishihara et al. | 436/47 |
| 6,822,741 B2 | 11/2004 | Aronkyto et al. | |
| 6,825,921 B1 | 11/2004 | Modlin et al. | |
| 7,202,392 B2 * | 4/2007 | Dotto | 800/3 |

FOREIGN PATENT DOCUMENTS

| | | |
|---|---|---|
| JP | H09-502520 A | 3/1997 |
| JP | 2002-48802 A | 2/2002 |
| JP | 2003-156500 A | 5/2003 |

* cited by examiner

AUTOMATED ANALYZER

This application is a Continuation of U.S. Ser. No. 10/862,507 filed on Jun. 7, 2004 now U.S. Pat. No. 7,381,370, which claims the priority to U.S. Provisional Application No. 60/488,336, filed Jul. 18, 2003.

RELATED APPLICATION

This application claims priority to U.S. patent application Ser. No. 60/488,336, filed Jul. 18, 2003.

FIELD OF THE INVENTION

The present invention relates to an apparatus for automatically processing a patient's biological fluid samples such as urine, blood serum, plasma, cerebrospinal fluid and the like. In particular, the present invention provides an automated system having multiple detectors for analysis of the samples according to one or more of a number of assay protocols.

BACKGROUND OF THE INVENTION

Various types of tests related to patient diagnosis and therapy can be performed by analysis of a sample taken from a patient's infections, bodily fluids or abscesses. These assays typically involve automated analyzers onto which vials containing patient samples have been loaded. The analyzer extracts the samples from the vials and combines the samples with various reagents in special reaction cuvettes or tubes. Frequently, the samples are incubated or otherwise processed before being analyzed. Analytical measurements are often performed using a beam of interrogating radiation interacting with the sample-reagent combination, for example turbidimetric, fluorometric, absorption readings or the like. The measurements allow determination of end-point or rate values from which an amount of analyte may be determined using well-known calibration techniques.

Although various known clinical analyzers for chemical, immunochemical and biological testing of samples are available, analytical clinical technology is challenged by increasing needs for improved levels of analysis. The improvement of analytical sensitivity continues to be a challenge. Furthermore, due to increasing pressures on clinical laboratories to reduce cost-per-reportable result, there continues to be a need for improvements in the overall cost performance of automated clinical analyzers. Often a sample to be analyzed must be split into a number of sample aliquots in order to be processed by several different analytical techniques using different analyzers. Sample analysis continuously needs to be more effective in terms of increasing assay throughput and increasing speed, as well as providing an increased number of advanced analytical options so as to enhance a laboratory's efficiency in evaluating patient samples. In particular, the results of a first battery of assays on a sample often dictate that a second battery of different assays be performed in order to complete or confirm a diagnosis, called reflux or add-on testing. In such an instance, the second battery of assays is often performed with a more sophisticated analytical technique than the first battery so that sample must be shuffled between different analytical laboratories. In addition to increased inefficiency, extra sample handlings increase the possibility of errors.

Automated clinical analyzers are typically controlled by software executed by a computer using software programs written in a machine language like on the Dimension® clinical chemistry analyzer sold by Dade Behring Inc, of Deerfield, Ill., and widely used by those skilled in the art of computer-based electromechanical control programming. Such a computer executes application software programs for performing assays conducted by the analyzer but it is also required to be programmed to control and track, among other items:

various analytical devices for performing 100+ different assays on different samples like blood, serum, urine and the like;

re-testing and add-on testing of samples when required by prior results;

the patient's identity, the tests to be performed, if a sample aliquot is to be retained within the analyzer;

calibration and quality control procedures;

an incoming and outgoing sample tube transport system;

inventory and accessibility of sample aliquots within an environmental chamber;

washing and cleaning reusable cuvettes;

reagent and assay chemical solution consumption along with time, and date of consumption of all reagents consumed out of each reagent container and assay chemical solutions consumed out of each vial container on a per reagent container, per calibration vial container, per Quality Control container, per assay, and per calibration basis, for specifically defined time periods; and, scheduling at least 1000 assays per hour.

From the above descriptions of the complex multiple operations conducted within a clinical analyzer, it is apparent that increasing the ability of a single analyzer to perform analytical tests using a relatively large number of different assay formats in a "user-friendly" manner presents much greater challenges than are encountered when an analyzer conducts, for example, only two different assay formats. However, within the clinical diagnostic field there is a continuing need for new and accurate analytical techniques that can be adapted for a wide spectrum of different analytes or be used in specific cases where other methods may not be readily adaptable. Convenient, reliable and non-hazardous means for detecting the presence of low concentrations of materials in liquids is desired. In clinical chemistry these materials may be present in body fluids in concentrations below 10.sup.-12 molar. The difficulty of detecting low concentrations of these materials is enhanced by the relatively small sample sizes that can be utilized. In developing an assay there are many considerations. One consideration is the signal response to changes in the concentration of analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as latex beads and liposomes, have also been utilized in assays. For example, in homogeneous assays an enzyme may be entrapped in the aqueous phase of a liposome labeled with an antibody or antigen. The liposomes are caused to release the enzyme in the presence of a sample and complement. Antibody or antigen-labeled liposomes, having water soluble fluorescent or non-fluorescent dyes encapsulated within an aqueous phase vesicle or lipid soluble dyes dissolved in the lipid bilayer of a lipid, have also been utilized to assay for analytes capable of entering into an immunochemical reaction with the surface bound antibody or antigen. Detergents have been used to release the dyes from the aqueous phase of the liposomes. Chemiluminescent labels offer exceptional sensitivity in ligand binding assays, but one or more chemical activation steps are usually needed. Fluorescent labels do not have this deficiency but are less sensitive.

U.S. Pat. Nos. 5,340,716 and 5,709,994 discloses a method for determining an analyte in a highly sensitive assay format known as a Luminescent Oxygen Channeled Immunoassay (LOCI) using a label reagent comprising a first specific binding pair member associated with a particle having a photosensitizer capable upon activation of generating singlet oxygen and a chemiluminescent compound capable of being activated by singlet oxygen such that upon activation of the photosensitizer, singlet oxygen is generated and activates the chemiluminescent compound, wherein the first specific binding pair member is capable of binding to the analyte or to a second specific binding pair member to form a complex related to the presence of the analyte; the photosensitizer is activated and the amount of luminescence generated by the chemiluminescent compound is detected and related to the amount of analyte in the sample.

U.S. Pat. No. 5,807,675 discloses a method for determining an analyte in a less sensitive assay format known as a Fluorescent Oxygen Channeled Immunoassay (FOCI) using a photosensitizer capable in its excited state of generating singlet oxygen, wherein the photosensitizer is associated with a first specific binding pair member in combination with a photoactive indicator precursor capable of forming a photoactive indicator upon reaction with singlet oxygen, wherein the photoactive indicator precursor is associated with a second specific binding pair member. The combination is irradiated with light to excite the photosensitizer, and in a final step, the fluorescence is measured and related to the amount of the analyte in the sample.

Homogeneous immunoassays in which it is unnecessary to separate the bound and unbound label have previously been described for small molecules. These assays include SYVA's FRAT assay, EMIT® assay, enzyme channeling immunoassay, and fluorescence energy transfer immunoassay (FETI); enzyme inhibitor immunoassays (Hoffman LaRoche and Abbott Laboratories): fluorescence polarization immunoassay (Dandlicker), among others. All of these methods have limited sensitivity, and only a few including FETI and enzyme channeling, are suitable for large multiepitopic analytes. Heterogenous immunoassays in which a separation step is required are generally useful for both small and large molecules. Various labels have been used including enzymes (ELISA), fluorescent labels (FIA), radiolabels (RIA), chemiluminescent labels (CLA), etc. Clinical analyzers in which such homogeneous and heterogenous immunoassays are commercially available and these are generally quite complex. See for example, U.S. Pat. Nos. 6,074,615 and 5,717, 148 and 5,985,672 and 5,635,364. From a consideration of patents such as these, it becomes obvious that many challenges are created when clinical analyzers having automated immunoassay systems are to be enhanced in capability with the additional automated ability to perform sensitive Luminescent Oxygen Channeled Immunoassays.

SUMMARY OF THE INVENTION

The analyzer of the present invention allows for various diagnostic assays to be performed on a single system, and provides for higher sensitivity as well as faster processing speeds. According to one aspect of the invention, an automated includes a plurality of cuvettes, each adapted to contain a reaction mixture including a sample and one or more reagents. The analyzer includes a LOCI reader adapted to detect luminescence of a reaction mixture in one or more of the cuvettes. One or more other detectors may also be included and are adapted to perform other analysis of a reaction mixture in one or more of the cuvettes or in a liquid flow-through cell. A cuvette transport mechanism is adapted to move the cuvettes to the detectors. The analyzer also includes a control mechanism adapted to control the detectors and the cuvette transport mechanism. Further aspects of the invention will be evident based on the claims that follow the detailed description.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
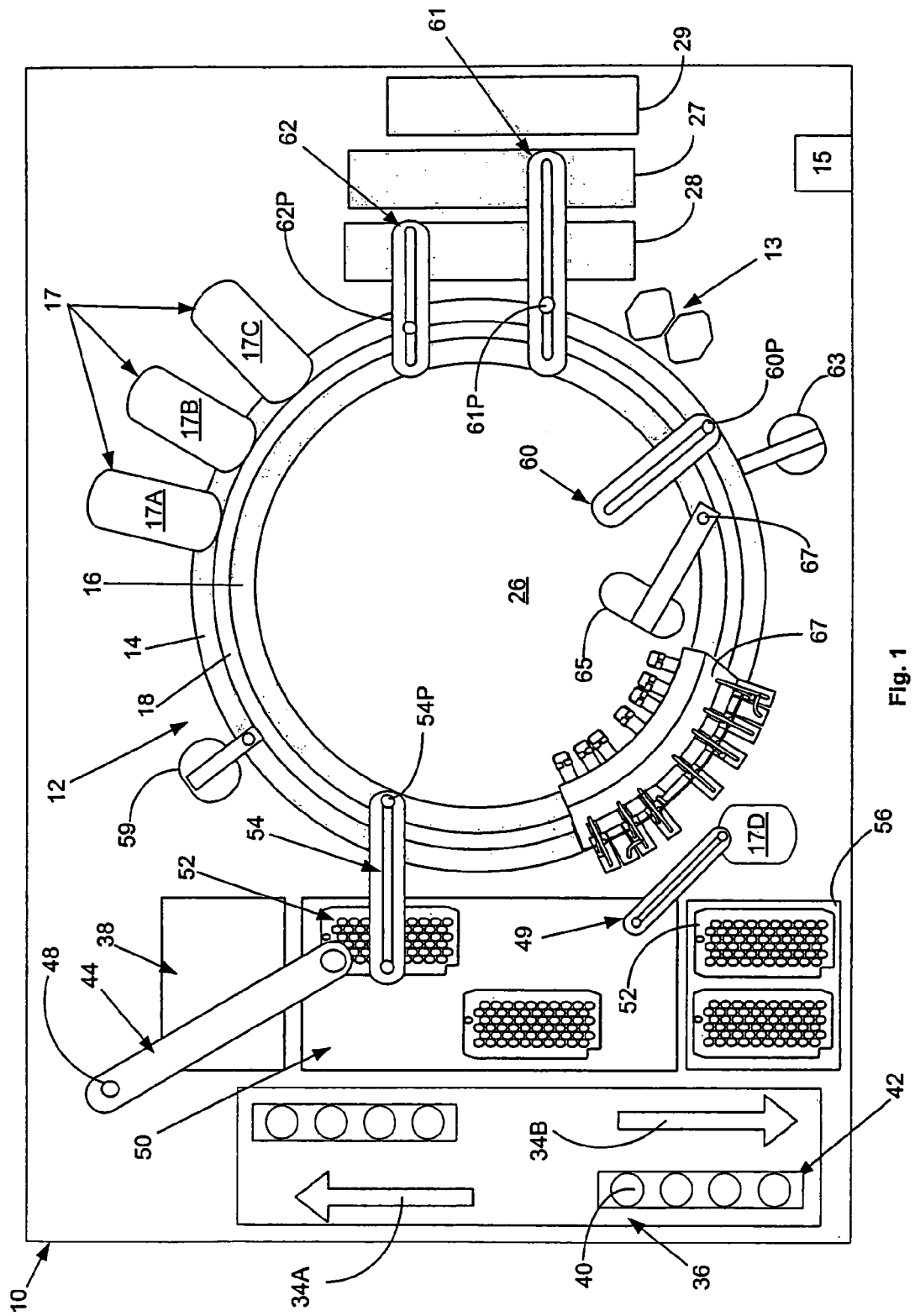
FIG. 1 is a schematic plan view of an automated analyzer illustrative of the present invention.
Figure 2:
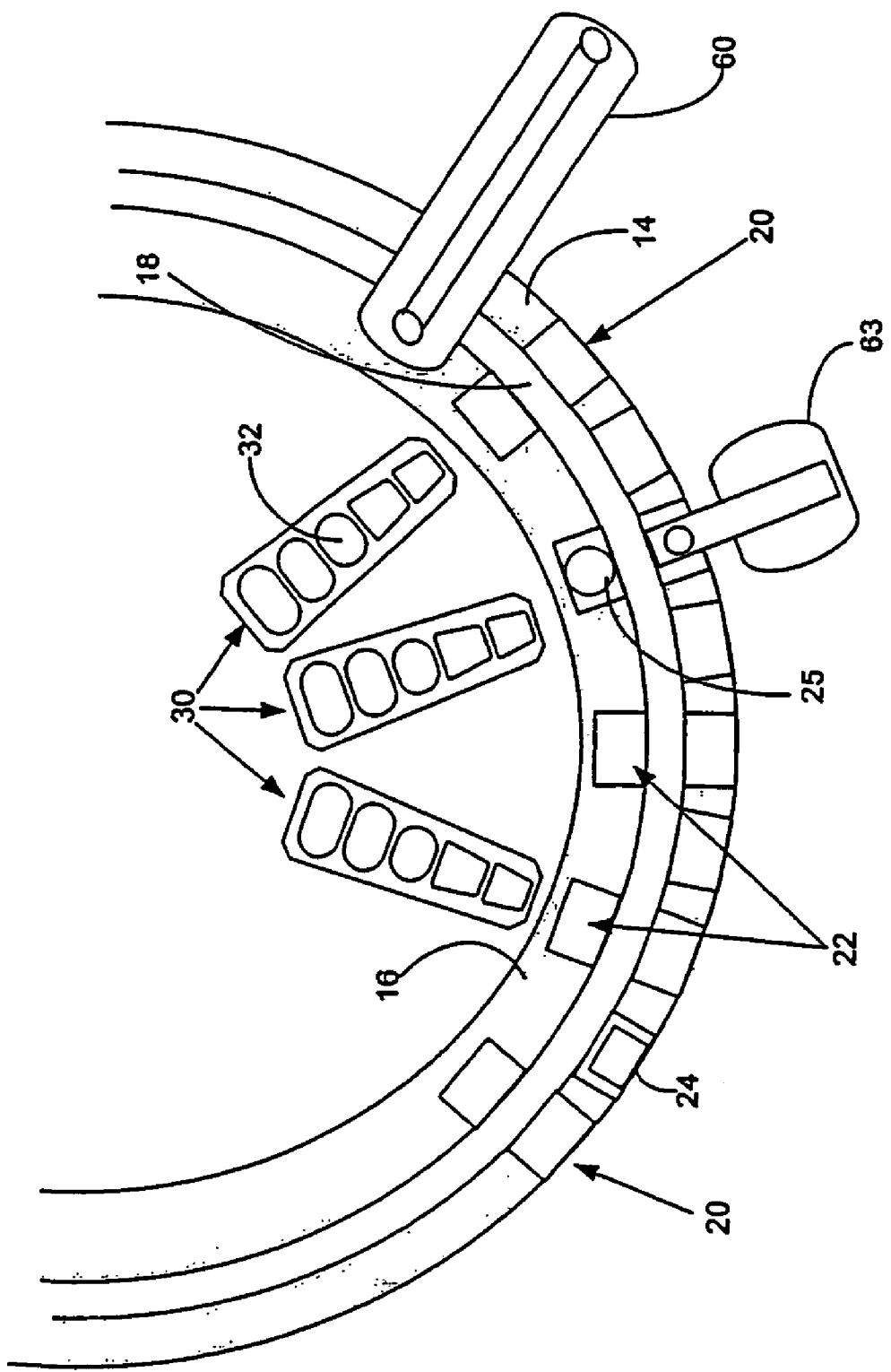
FIG. 2 is an enlarged schematic plan view of a portion of the analyzer of FIG. 1.

FIG. 1, taken with FIG. 2, shows schematically the elements of an automatic chemical analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 like disclosed in co-pending application Ser. No. 09/949,132 assigned to the assignee of the present invention and containing various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise cyclic movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within cuvettes 24 and reaction vessels 25.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means within analyzer 10. The analyzer 10 according to the present invention includes multiple detection units 17A, 17B, 17C and 17D, each including one or more detectors. In a preferred embodiment, each detection unit 17A, 17B, 17C and 17D, is adapted to perform different measurements and follow various analysis protocols that the other detection units. The diversity of detectors allows multiple types of tests to be run on the same system, thereby increasing the likelihood that an analyte can be determined by an assay that is most appropriate for that particular analyte, e.g, an assay that is highly specific for the analyte, is accomplished in a reasonable period of time, and is cost effective. The samples and reaction mixture may be analyzed in the cuvettes 24, 25 while in their respective carousels 14, 16, or may be moved into the detection units 17A, 17B, 17C and 17D, by a conventional cuvette transporter (not shown).

Figure 12:
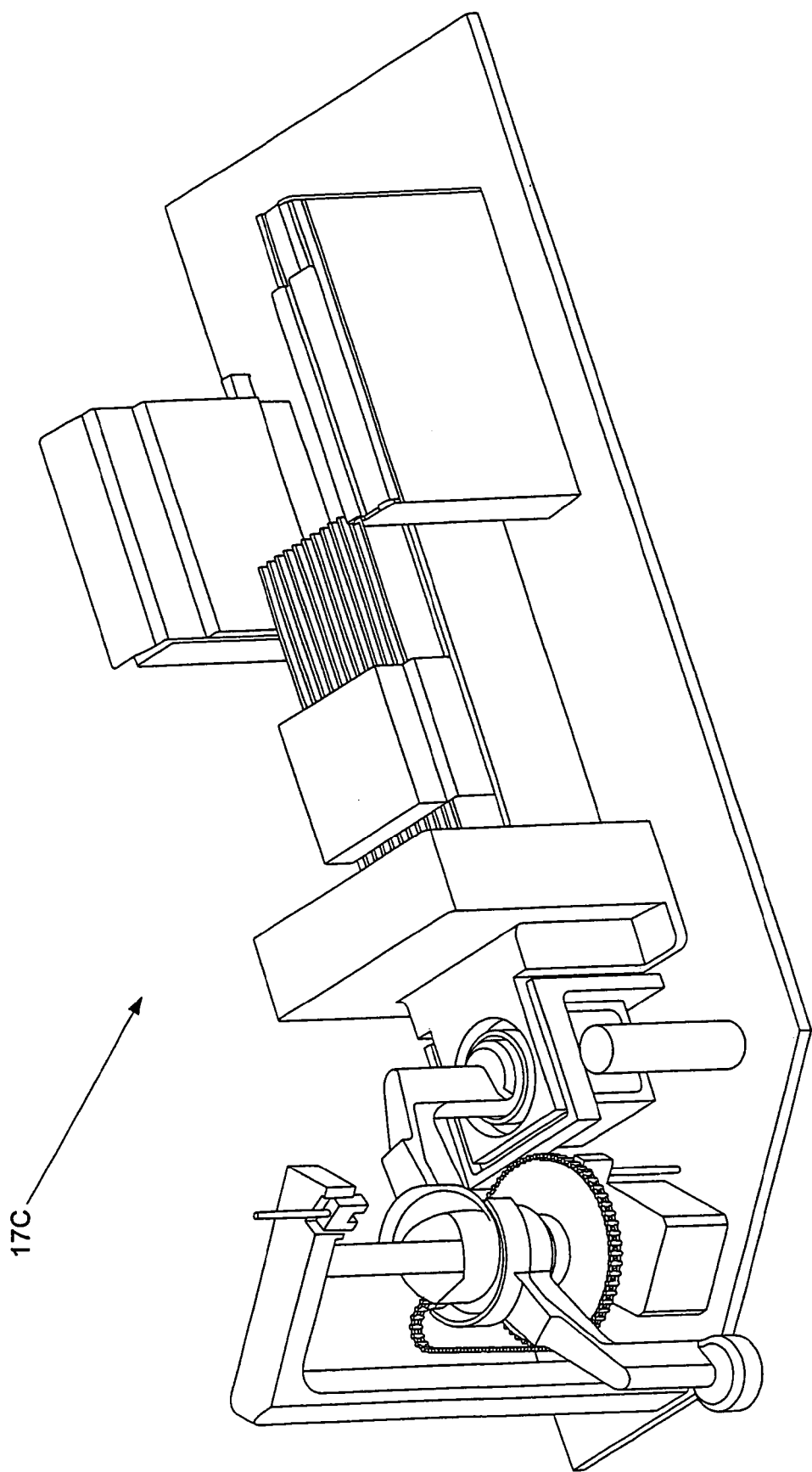

In the embodiment shown in FIG. 1, the analyzer 10 includes a detection unit 17C exemplified by FIG. 12 which includes detector adapted to detect luminescence of a reaction mixture in one of the reaction vessels 25. Preferably, the detector is a conventional luminometer 17C or a chemiluminometer 17C. More preferably, the luminometer is configured as a LOCI reader 17C, that is, the luminometer preferably is configured to allow the analyzer 10 to perform luminescent oxygen channeling immunoassays ("LOCI"). LOCI assays provide significant advantage over many conventional immunoassays run on automated analyzers because LOCI is highly specific and can be performed without many of the time-consuming separation steps typically associated with such conventional immunoassays. Furthermore, LOCI is a reliable method and results in less analyzer down time. As described previously, LOCI assays involve measurement of luminescence from a chemiluminescent compound which associates with a photosensitizer in the presence of a particular analyte. Optimally, the chemiluminscent compound is photochemically activated by singlet oxygen. The singlet oxygen is preferably produced by irradiating the photosensitizer. The light emitted by the chemiluminescent compound can be measured quantitatively to determine the amount of analyte. Accordingly, the reagents stored in the storage area 26 preferably include a photosensitizer and a complementary chemiluminescent compound. The detection unit 17C preferably is surrounded by an environmental chamber (shown in dotted lines) which is adapted to shield the detection unit 17C and the sample being analyzed from being exposed to environmental light, which would be detrimental to the assay. Furthermore, the cuvettes 25 and/or the accompanying carousel 16 may be configured to shield light sensitive reagents or reaction mixture from surrounding environmental light.

The remaining detection units 17A, 17B, 17D, may also be adapted to detect luminescence, however, they are preferably adapted to perform different, non-luminescence based analyses in order to optimize and diversify the capabilities of the analyzer. For example, detection unit 17A may include a photometer or a turbidometer. A suitable photometer is used as part of the Dimension® clinical chemistry analyzer manufactured and sold by Dade Behring Inc. of Deerfield, Ill. Detection unit 17B may include yet a different type of detector, such as a nephelometer. Furthermore, detection unit 17D preferably includes yet another, different type of detector, such as an ion selective electrode.

Computer 15 is interlinked using known interface software applications with a Laboratory Information System (LIS) and/or a Hospital Information System (HIS) so that information concerning patients, patient assay requests, assay results, analyzer status, and the like, may be immediately accessible as needed by laboratory personnel. Computer 15 includes an operator interface module typically comprising a keyboard and monitor or a flat-panel touch viewing screen or the like, on which information about the operational status of analyzer 10 as described herein may be called up and displayed or which may be automatically displayed like in the instance of a malfunction within analyzer 10.

Figure 3:
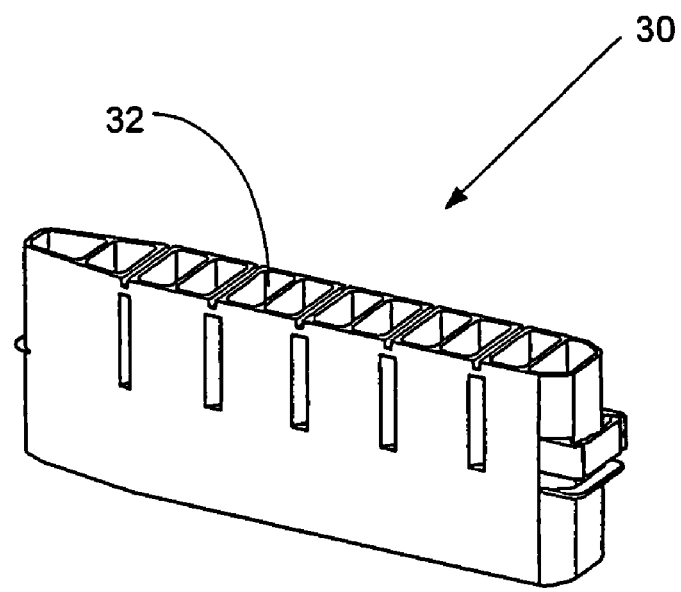
FIG. 3 is a perspective view of a reagent container useful in the analyzer of FIG. 1.
Figure 3A:
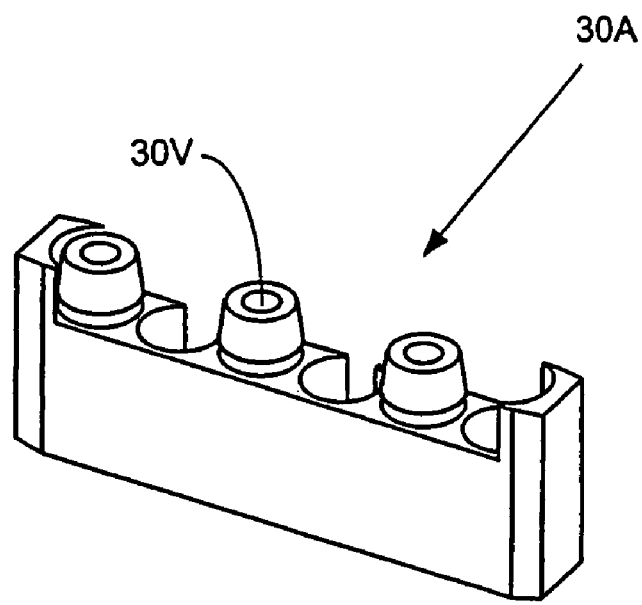
FIG. 3A is a perspective view of a calibration solution vial container useful in the analyzer of FIG. 1.

Temperature-controlled reagent storage areas 26, 27 and 28 store a plurality of multi-compartment elongate reagent containers 30 like that illustrated in FIG. 3 and containing reagents necessary to perform a given assay within a number of wells 32, each well containing as much as 3.4 mL of a given reagent. Container 30 has features to enable analyzer 10 to automatically determine whether a reagent container 30 is new and unused or whether the reagent container 30 has been previously used and possibly become contaminated whenever a reagent container 30 is initially placed onto an analyzer. FIG. 3A shows a calibration vial container 30A containing calibration solutions of known analyte concentrations in calibration solution vials 30V, the solutions being to conduct well-know calibration and quality control procedures within analyzer 10. Calibration vial containers 30A are also inventoried upon analyzer 10 within reagent storage areas 26, 27 and 28

A bi-directional incoming and outgoing sample tube transport system 36 having input lane 34A and output lane 34B transports incoming individual sample tubes 40 containing liquid specimens to be tested and mounted in sample tube racks 42 into the sampling range of a liquid sampling probe 44, like disclosed in co-pending application Ser. No. 10/623, 311 assigned to the assignee of the present invention. Liquid specimens contained in sample tubes 40 are identified by reading bar coded indicia placed thereon using a conventional bar code reader to determine, among other items, a patient's identity, tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 4:
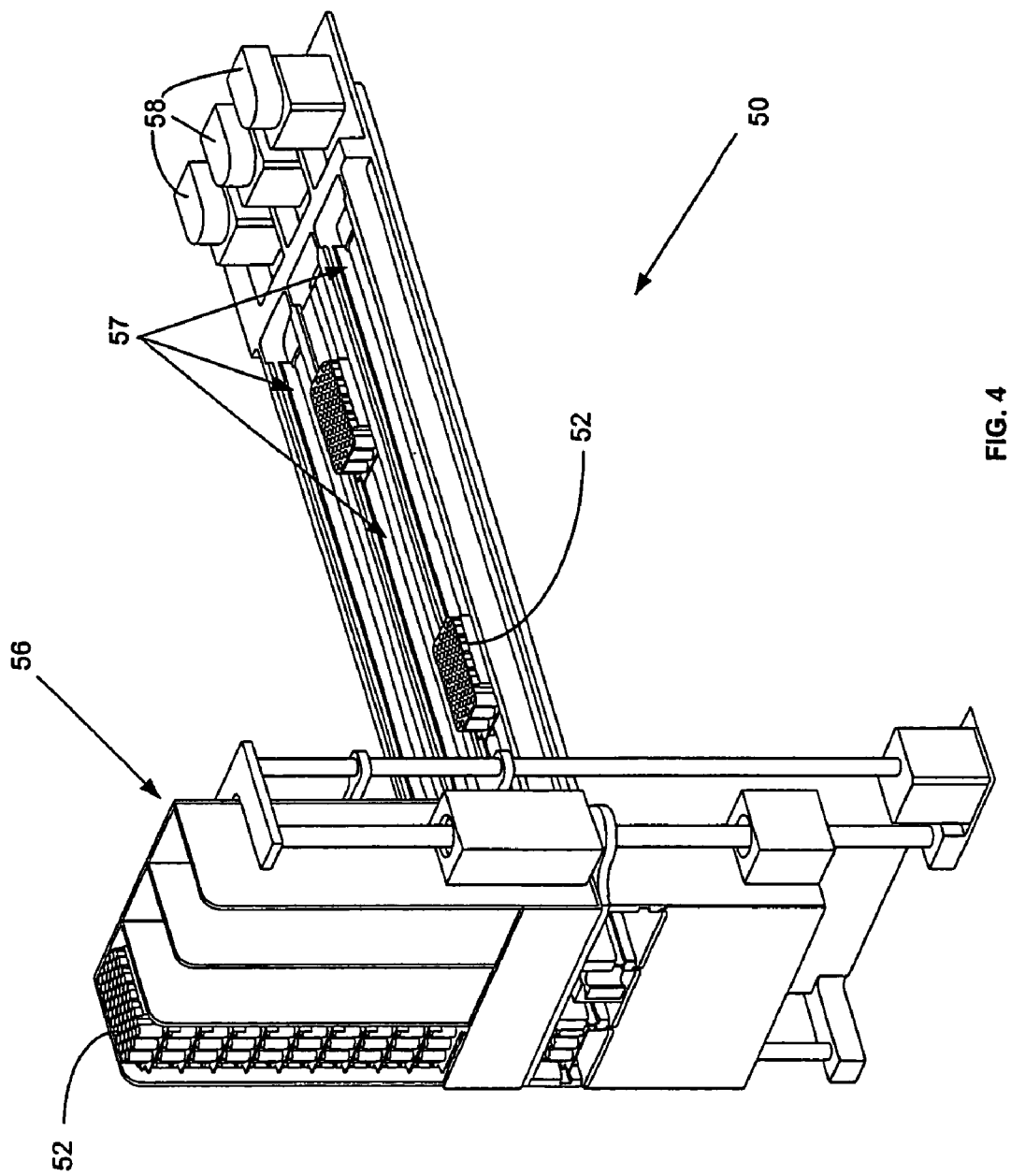
FIG. 4 is a perspective view of an aliquot vessel array storage and handling unit useful in the analyzer of FIG. 1.
Figure 4A:
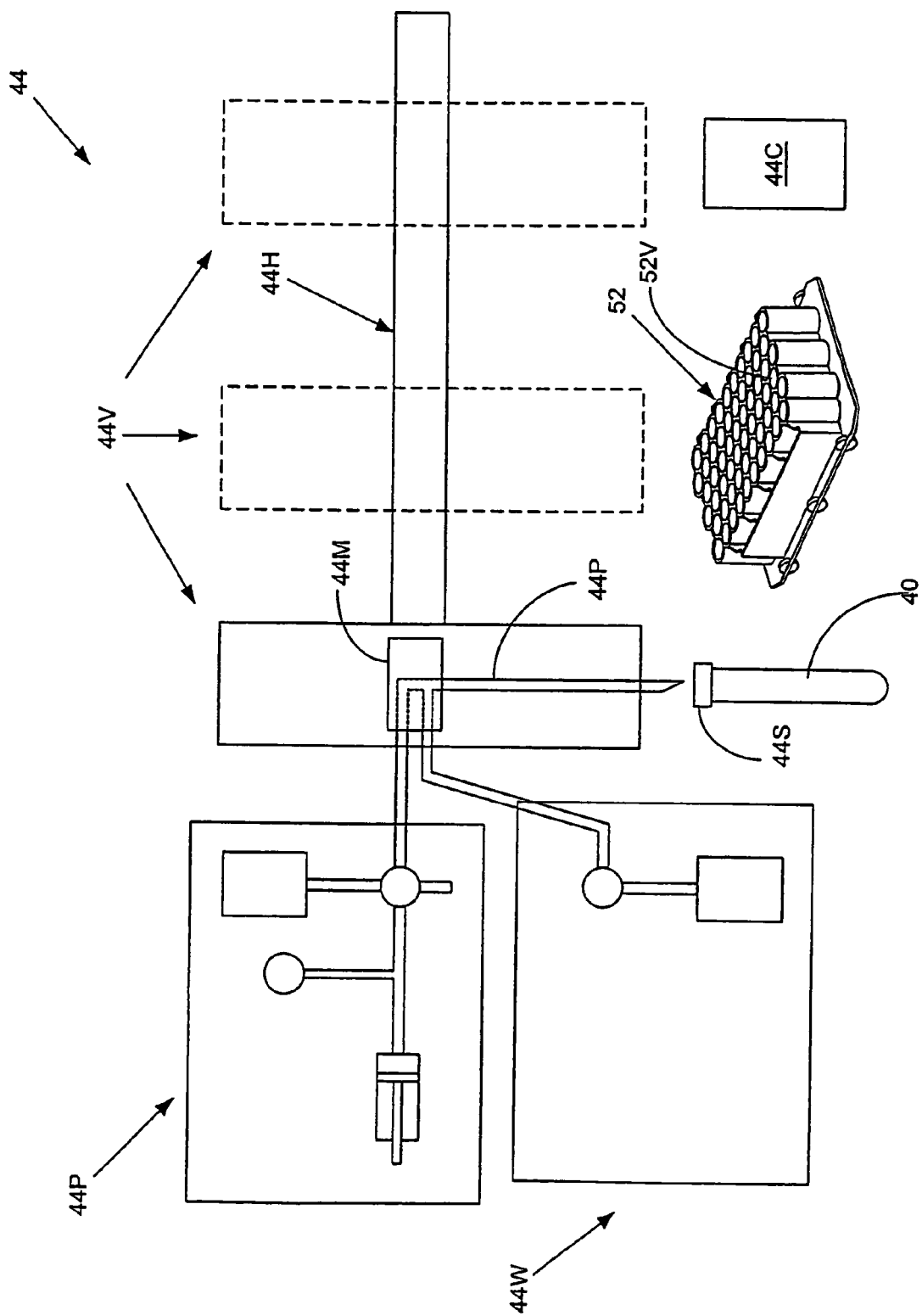
FIG. 4A is a sampling probe useful in the analyzer of FIG. 1.
Figure 5:
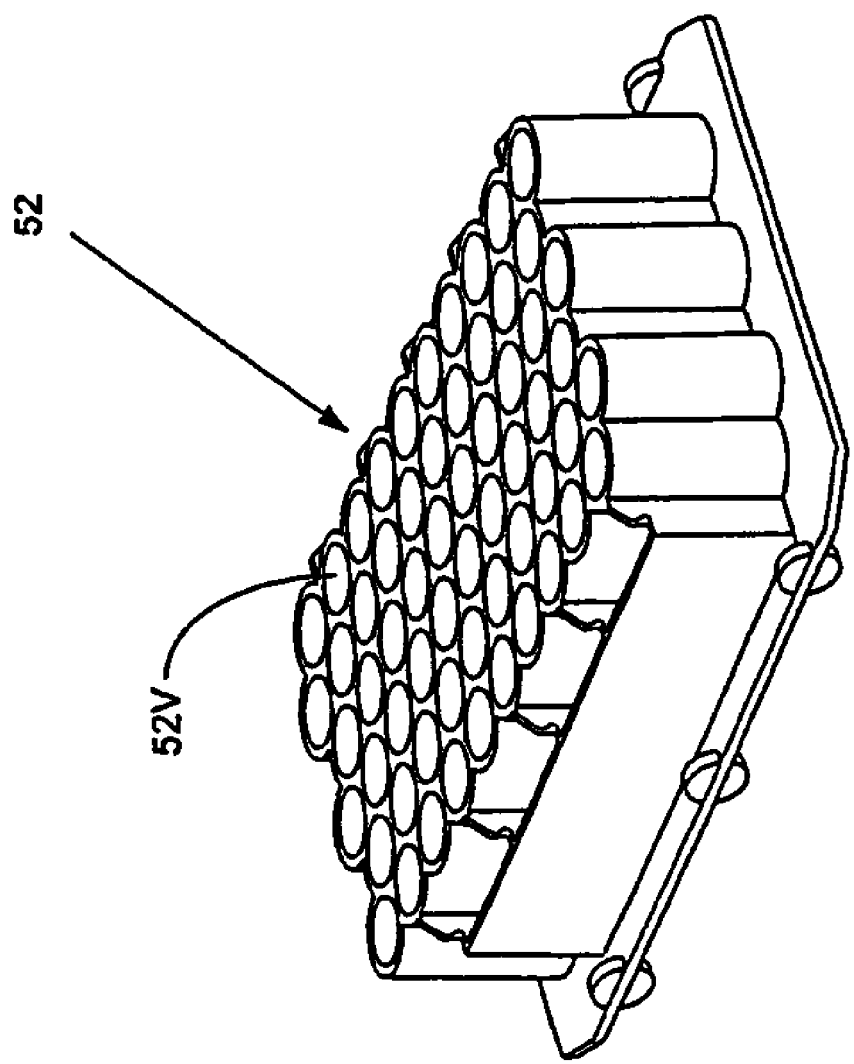
FIG. 5 is an aliquot vessel array useful in the analyzer of FIG. 1.

Sampling probe 44 comprises a translatable liquid sampling probe 48 so that movement of sampling arm 44 describes an arc intersecting the sample tube transport system 36 and an aliquot vessel array transport system 50, as seen in FIG. 4. Sampling probe 44, as seen in FIG. 4A, comprises a Horizontal Drive 44H, a Vertical Drive 44V, a Wash Module 44W, a Pump Module 44P and a Cleansing Module 44C having the primary functions described in Table 1 below, so that sampling probe 44 is operable to aspirate liquid sample from sample tubes 40 and to dispense an aliquot sample into one or more of a plurality of vessels 52V in aliquot vessel array 52, as seen in FIG. 5, depending on the quantity of sample required to perform the requisite assays and to also provide for a sample aliquot to be retained by analyzer 10 within environmental chamber 38.

TABLE 1

| Module | Primary Functions |
| --- | --- |
| Horizontal Drive 44H | 1. Position Vertical Drive 44V over sample fluid tubes 40 on a rack 38, over individual vessels 52V of aliquot vessel arrays 52 and over Cleansing Module 44C |
| Vertical Drive 44V | 1. Position a sampling probe 44P at vertical positions for aspiration and dispense operations<br>2. Drive probe 44P through the stopper 44S of a sample fluid tube 40<br>3. Determine liquid level of sample fluid in sample tube 40<br>4. Monitor aspiration quality |
| Wash Module 44W | 1. Remove contamination from probe 44C with liquid cleansing solutions |
| Cleansing Module 44C | 1. Cleansing interior and exterior surfaces of sample fluid probe 44P |
| Pump Module 44P | 1. Aspirate and dispense sample fluid<br>2. Wash probe 44P |
| Wash Manifold 44M | 1. Connect Wash Module 44W and Pump Module 44P to probe 44P |

Environmental chamber 38 is operated by computer 15 to ensure that the same patient specimen is tested a second time following a previous first testing. For reasons of processing efficiency, it is sometimes desirable to automatically reprocess a sample aliquot that has been retained in within environmental chamber 38 for a predetermined period of time. Incoming samples to be tested may be identified by bar coded indicia placed on sample tubes 40 to determine if a sample aliquot is to be retained, and if so, for what period of time. In addition to a first sample aliquot taken from a patient's specimen to be tested, a second sample aliquot is also taken from the same patient's specimen and is retained in within environmental chamber 38. If it becomes desirable to re-test or additionally test a patient's sample some period of time after tests on the first sample aliquot are completed, reported, and analyzed by a physician, the second sample aliquot may be quickly removed from within environmental chamber 38 and tested on analyzer 10, thereby saving time as well as providing for the exact same patient specimen to be tested.

Figure 10:
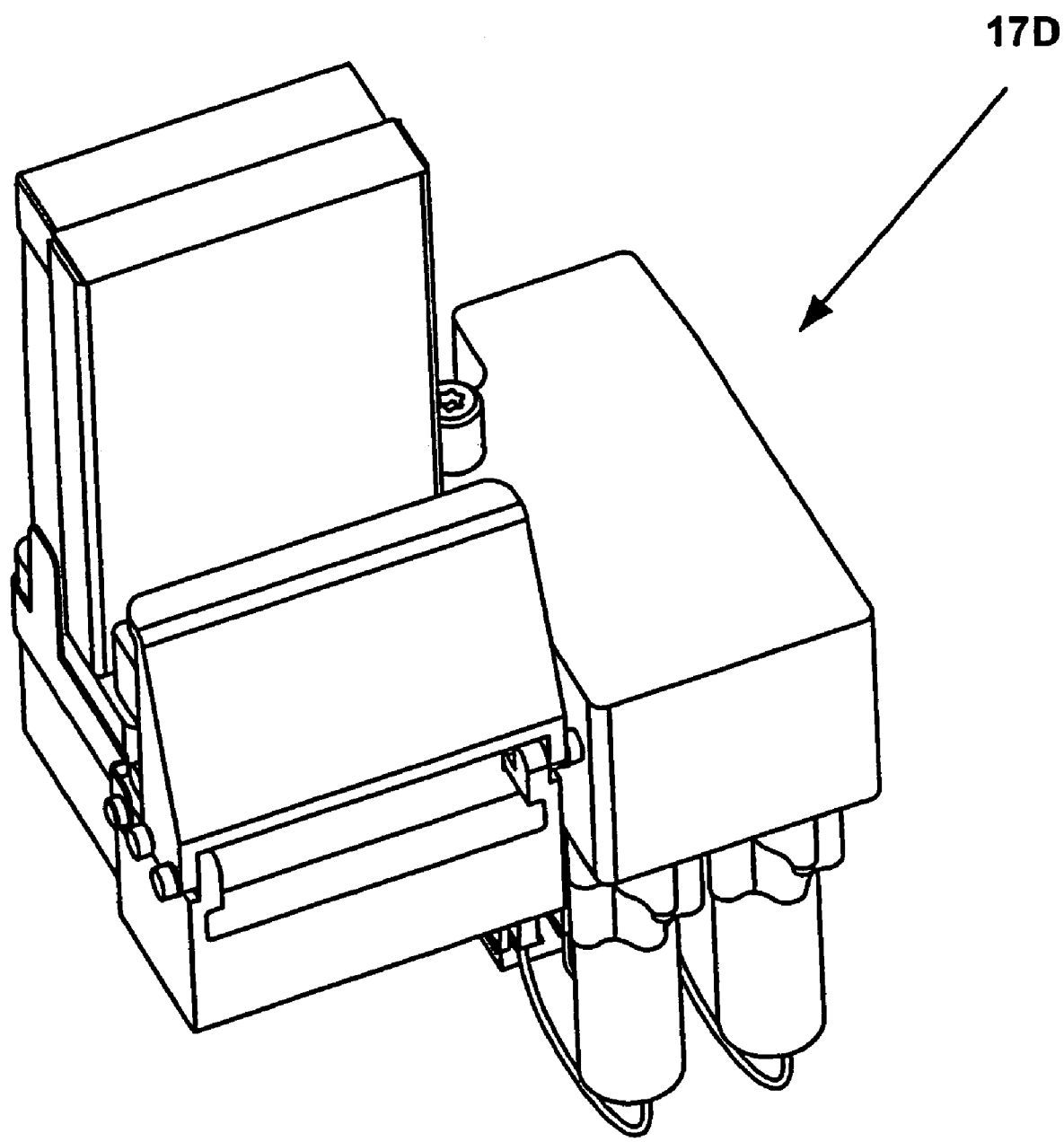
FIG. 10 is a perspective view of an ion selective electrode measuring device useful within the present invention.

A conventional ion selective electron measuring station 17D equipped with a conventional ion selective electron probe 49 may be conveniently located proximate aliquot vessel array transport system 50 in order to conduct ionic analyte measurements on sample aliquots aspirated from vessels 52V by probe 49 and dispensed into the ion selective electron measuring station 17D, seen in FIG. 10.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60, 61 and 62 each comprising at least one conventional liquid reagent probe, 60P, 61P and 62P, respectively, are independently mounted and translatable between reagent storage areas 26, 27 and 28, respectively. Probes 60P, 61P and 62P are conventional mechanisms for aspirating reagents required to conduct specified assays at a reagenting location from wells 32 in an appropriate reagent container 30, the probes 60P, 61P and 62P subsequently being shuttled to a reagent dispensing location where reagent(s) are dispensed into reaction cuvettes 24. Probes 60P, 61P and 62P are also used for aspirating calibration and control solutions from calibration solution vials 30V as required to conduct calibration and control procedures necessary to ensure proper operation of analyzer 10, the probes 60P, 61P and 62P subsequently being shuttled to a calibration solution dispensing location where solutions(s) are dispensed into reaction cuvettes 24 and analyzed by analyzing means 17.

Figure 4B:
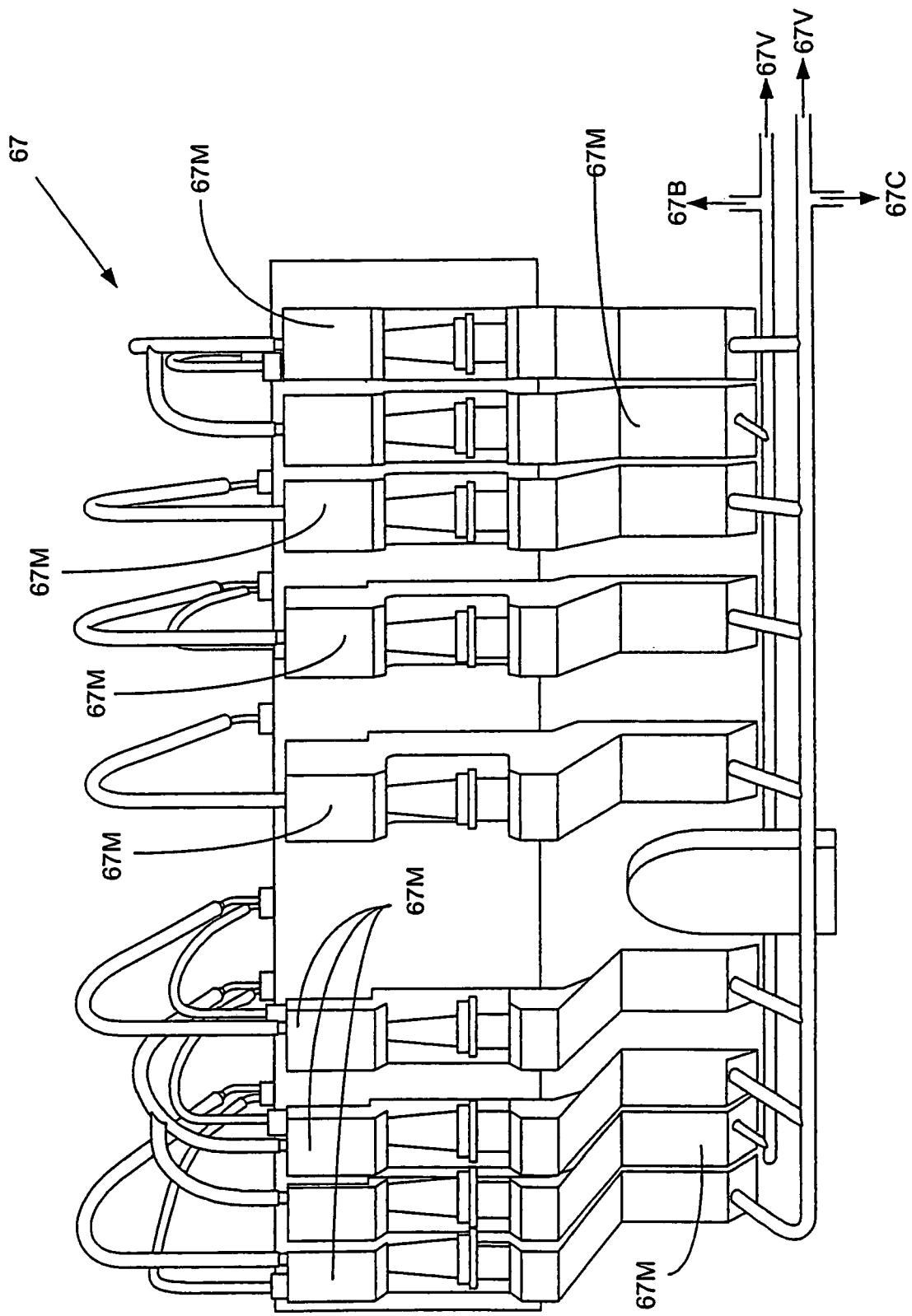
FIG. 4B is a wash station useful in the analyzer of FIG. 1.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 65. In operation, used cuvettes 24 in which an assay has been finally conducted, are washed and dried in a wash station 67 like disclosed in co-pending application Ser. No. 10/623,360 assigned to the assignee of the present invention. Computer 15 operates wash station 67 so that a used reaction cuvette 24 is cleansed so that whenever certain "exceptional" assays are scheduled to be next performed in a reaction cuvette 24, the used reaction cuvette 24 is automatically subjected to an additional cleansing or cleaning operation, the terms "cleaning and cleansing" including washing, rinsing, and drying. This selective cleaning of a used reaction cuvette 24 is partially achieved by providing a number of washing and drying manifolds 67M, like seen in FIG. 4B, each of which is independently selectively activated to perform or not perform a cleansing operation, depending upon the identity of the assay scheduled to be next performed in that reaction cuvette 24. Further, wash station 67 is operated by computer 15 so that biohazard waste residues from biochemical reactions in a cuvette 24 are segregated from chemical waste residues from chemical reactions in a cuvette 24 and are safely disposed into secure biochemical waste storage 67B and chemical waste storage 67C by means of vacuum lines 67V.

Subsequent assays are conducted in cleaned used cuvettes 24 unless dictated otherwise for reasons like disclosed in co-pending application Ser. No. 10/318,804 assigned to the assignee of the present invention. Computer 15 is programmed to determine not to reuse a cleaned used reaction cuvette 24 whenever an assay scheduled to be next performed in a cleaned used reaction cuvette 24 might be adversely affected by any contaminants remaining from the assay previously performed in a cleaned used reaction cuvette 24. In addition, computer 15 may operate analyzer 10 so that whenever certain assays are scheduled to be next performed in a cleaned used reaction cuvette 24, the cleaned used reaction cuvette 24 is automatically removed, discarded, and replaced with a fresh, unused reaction cuvette 24. Computer 15 may optionally control analyzer 10 so that whenever an assay is scheduled to be next performed in a cleaned used reaction cuvette 24, and the same assay was previously performed in the cleaned used reaction cuvette 24 and the assay results were outside normal test ranges, the cleaned used reaction cuvette 24 would be automatically removed, discarded, and replaced with a fresh, unused reaction cuvette 24. Cuvette unload station 59 is adapted to remove unusable reaction cuvettes 24 from cuvette ports 20 again using a translatable robotic arm 65 like seen on load stations 61 and 63.

Figure 6:
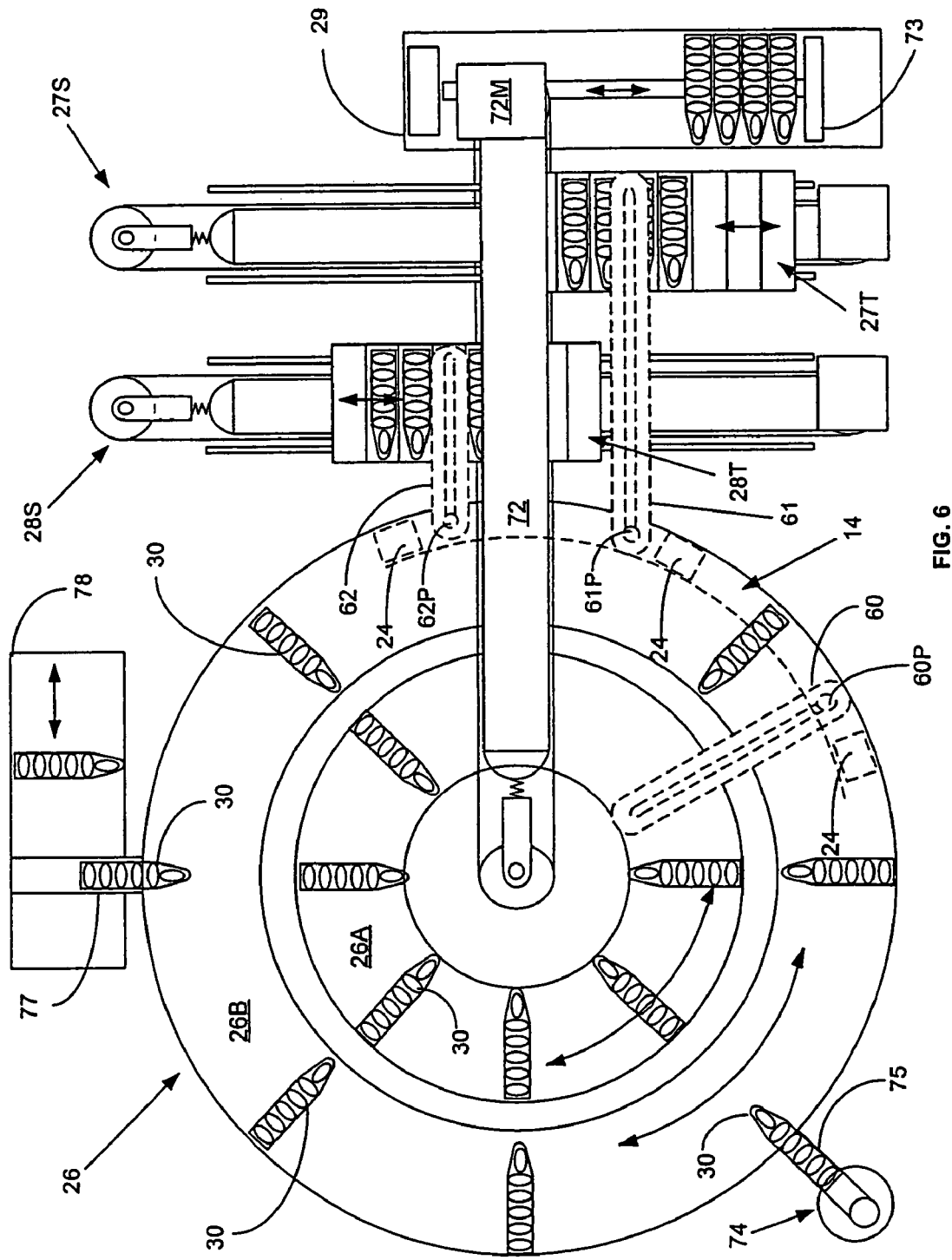
FIG. 6 is a schematic plan view of a container transport system useful in the analyzer of FIG. 1.

In order to re-supply assay reagents and calibration solutions as they are exhausted by assay demand, analyzer 10 includes a single, bi-directional linear container shuttle 72 illustrated in FIG. 6 and adapted to remove reagent containers 30 and calibration vial containers 30A from a container loading tray 29 having a motorized rake 73 that automatically locates containers 30 and 30A at a loading position beneath container shuttle 72. Shuttle 72 is further adapted to dispose a reagent container 30 or a calibration vial container 30A into slots in at least one slotted reagent container tray 27T or 28T within reagent storage areas 27 or 28, respectively. In a similar fashion, shuttle 72 is even further adapted to remove reagent containers 30 or calibration vial containers 30A from reagent container trays 27T and 28T and to dispose such reagent containers 30 or calibration vial containers 30A into either of two concentric reagent carousels 26A and 26B within reagent storage area 26. Shuttle 72 is also adapted to move reagent containers 30 and calibration vial containers 30A between the two concentric reagent carousels 26A and 26B.

As indicated by the double-headed arc-shaped arrows, reagent carousel 26A may be rotated in both directions so as to place any particular one of the reagent containers 30 or calibration vial containers 30A disposed thereon beneath reagent aspiration arm 60. Although reagent carousel 26B may also contain reagent containers 30 and calibration vial containers 30A accessible by reagent aspiration arms 60 and 62, carousel 26B is preferably designated only for storing excess inventory of reagent containers 30 and calibration vial containers 30A. Any one of the reagent containers 30 disposed in reagent container trays 27T and 28T may be located at a loading position beneath container shuttle 72 or at a reagent aspiration location beneath aspiration and dispensing arms 61 and 62, respectively, by reagent container shuttles 27S and 28S within reagent storage areas 27 and 28, respectively. Reagent aspiration arms 60 and 62 are shown in dashed lines to indicate that they are positioned above the surfaces of reagent containers 30 inventoried in carousel 26B, and reagent container trays 27T and 28T, respectively.

Reaction cuvettes 24 supported in outer cuvette carousel 14 are also both shown in dashed lines to indicate that they are positioned above the surfaces of reagent containers 30. FIG. 6 also shows a reagent preparation station 74 connected to reagent operation carousel 26B by means of a first reagent container transfer device 75. Reagent preparation station 74 is adapted to perform a number of reagent preparation operations like chemical additions, re-mixing, hydrating dry reagent powders and the like as may be required. In addition, a motorized belt shuttle 78 connected to reagent operation carousel 26B by means of a second reagent container transfer device 77, thereby enabling an exchange of reagent containers 30 between similarly equipped analyzers. A container shuttle system like seen in FIG. 6, is described in co-pending U.S. patent Ser. No. 10/623,310, assigned to the assignee of the present invention.

Figure 7:
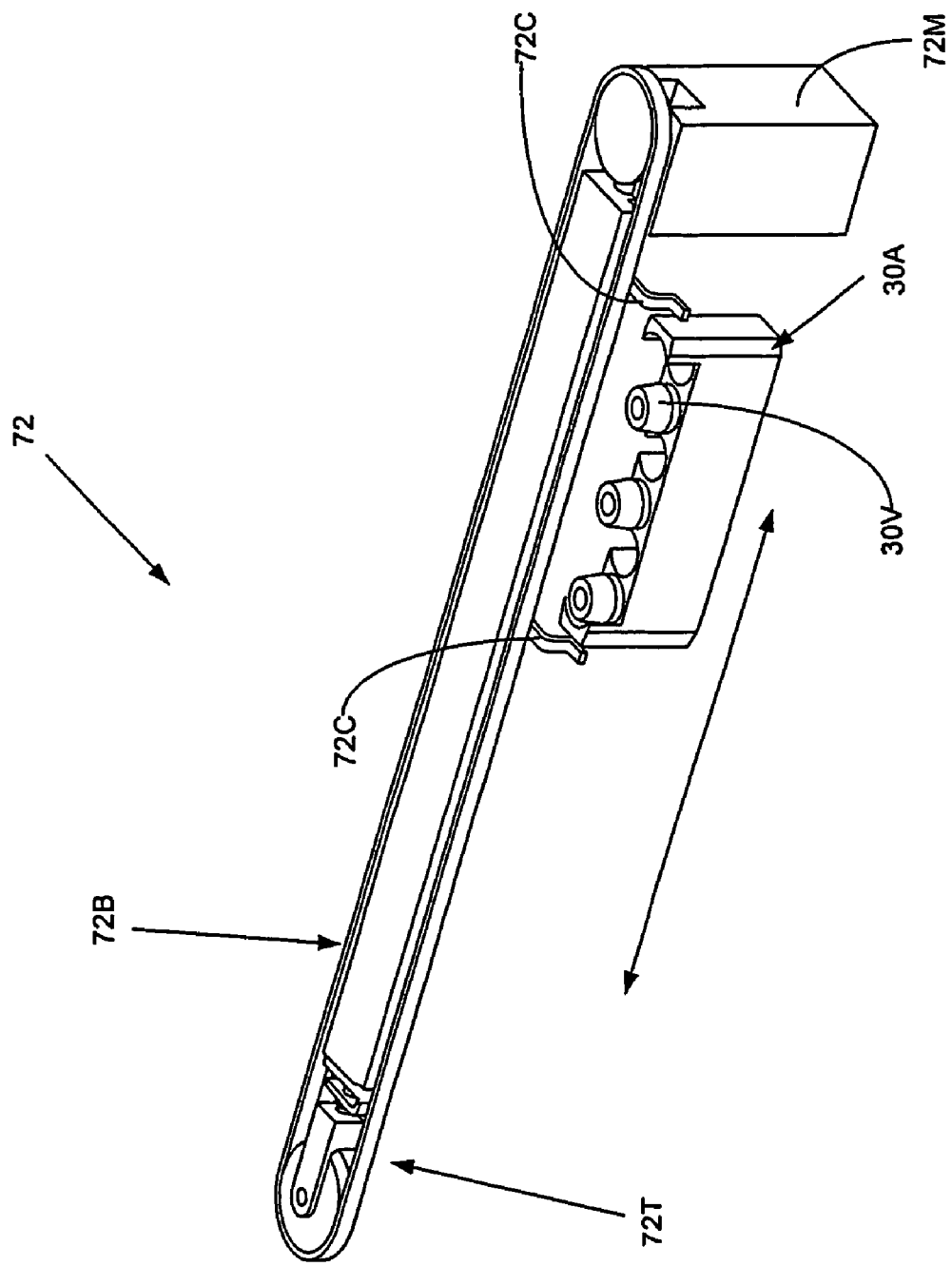
FIG. 7 is a perspective view of a container shuttle useful in the analyzer of FIG. 1.
Figure 8:
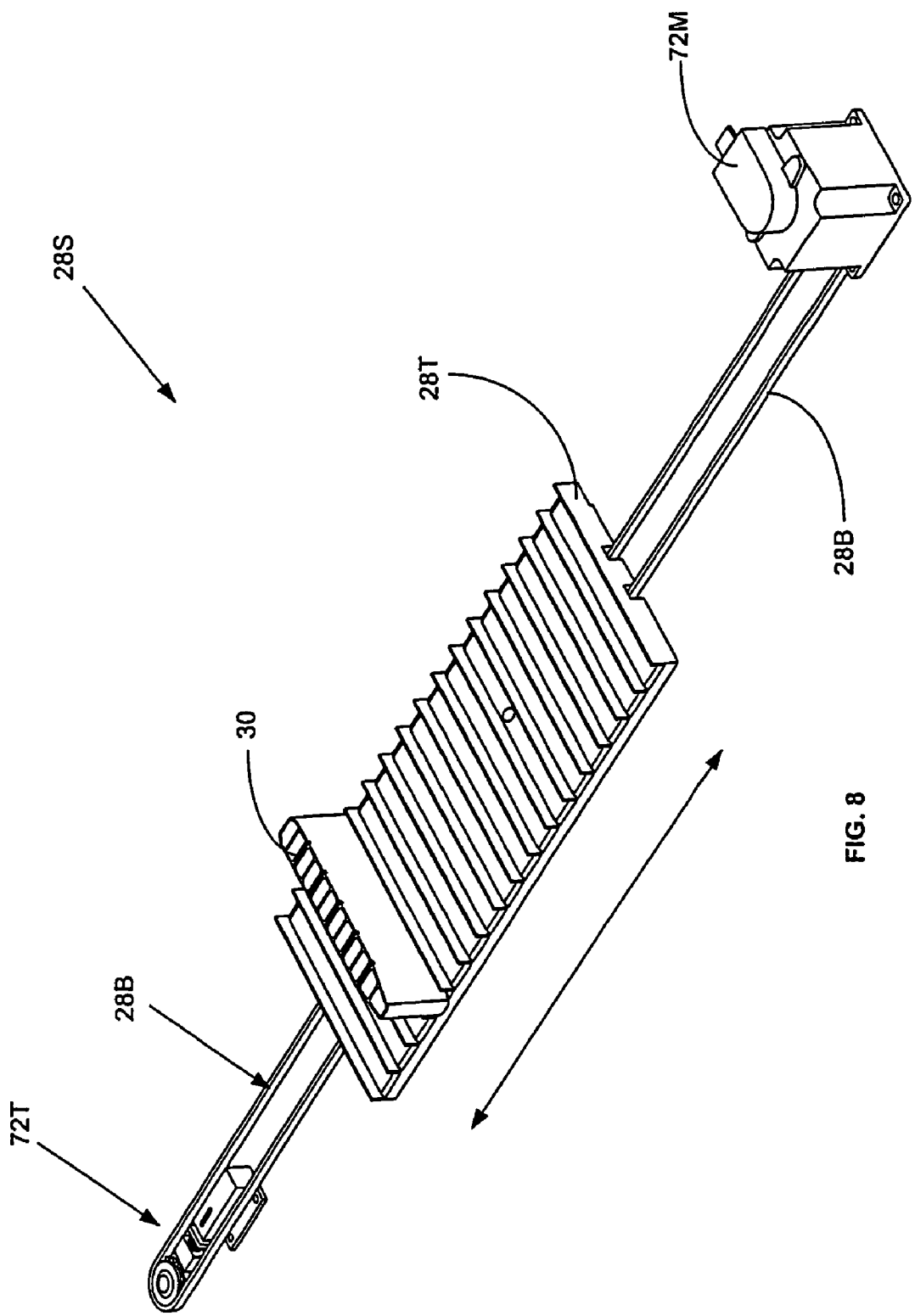
FIG. 8 is a perspective view of a container tray shuttle useful in the analyzer of FIG. 1.

Container shuttle seen in FIG. 7 is adapted to automatically compensate for unknown changes in length of a drive belt 72B driven by motor 72M by an automated tensioner 72T, disclosed in co-pending application Ser. No. 10/623,311 and assigned to the assignee of the present invention, and adapted to maintain a constant tension on the drive belt 72B regardless of rapid changes in its driving direction so that reagent containers 30 and calibration vial containers 30A attached thereto by clamps 72C may be accurately positioned along the direction of drive belt 72B, as indicated by the double-ended arrow, and disposed at their intended location beneath reagent container shuttle 72 or within storage areas 26, 27 or 28 as drive belt 72B wears. Reagent container shuttles 27S and 28S are similar in design to one another, and as seen in FIG. 8, include a reagent container tray 28T secured to one leg of a drive belt 28B so that tray 28T is free to be driven to and from along the direction of drive belt 28B, as indicated by the double-ended arrow. Consequently, reagent containers 30 within slots in tray 28T may be automatically positioned at a pick-up location beneath container shuttle 72.

From the preceding description of analyzer 10, it is clear to one skilled in the art that the capabilities of analyzer 10 under the control of computer 15 include the ability to automatically to move reagent containers 30 and calibration vial containers 30A between container loading tray 29, reagent container trays 27T and 28T, and reagent carousels 26A and 26B. By means of shuttles 27S and 28S, analyzer 10 is further capable of moving reagent containers 30 and calibration vial containers in reagent container trays 27T and 28T to appropriate aspiration locations by probes 61P and 62P, respectively, (or to a loading location beneath shuttle 72) so that in combination with the capability of reagent carousels 26A and 26B to place any reagent container 30 or calibration vial container 30A beneath reagent aspiration arms 60P, 61P and 62P. Analyzer 10 thus includes an automated random access reagent and calibration solution re-supply system with the flexibility to position a large number of different reagents and calibration solutions at different aspiration locations.

A key factor in maintaining an optimum assay throughput within analyzer 10 is the ability to timely re-supply reagent containers 30 into reagent storage areas 26, 27 and 28 before the reagents contained therein become exhausted. Similarly important is the ability to timely re-supply calibration and Quality Control solutions in vial containers 30A before the solutions contained therein become exhausted so that calibration and control procedures may be conducted as required, whether this be based on the basis of time between calibrations or number of assays performed since an immediately previous calibration or number of assay results outside normal ranges, or changes in the performance of the analyzer. This challenge may be met by timely equipping analyzer 10 with additional requisite calibration and Quality Control solutions used in calibration and control procedures and called standard chemical solutions herein for convenience, before they become exhausted, thereby maintaining assay throughput of analyzer 10 uninterrupted.

In order to maintain continuity of assay throughput, computer 15 is programmed to track reagent and assay chemical solution consumption along with time, and date of consumption of all reagents consumed out of each reagent container 30 and assay chemical solutions consumed out of each vial container 30A on a per reagent container, per calibration vial container, per Quality Control container, per assay, and per calibration basis, for specifically defined time periods. As disclosed in co-pending application Ser. No. 10/622,435 and assigned to the assignee of the present invention, computer 15 is programmed to make an inventory demand analysis for specifically defined time periods so as to determine future assay inventory demands for the specifically defined time periods and display to an operator on a display viewing screen 15S like illustrated in FIG. 9 a list of all of the reagent containers 30 and calibration/Quality Control vial containers 30A that will be needed in the future in a timely manner prior to the actual need of said reagent container 30 and calibration/Quality Control vial containers 30A.

A very simplified illustration of the analysis made by computer 15 may be found in Table 1, wherein an average assay demand is conducted on Monday, using the most recent historical Tuesday-specific assay demand for the four previous Tuesdays, for Total CO2, Creatinine, and BUN is 1255, 1140, and 1050, respectively. In view of the number of assays that may be conducted in single different reagent containers 30 containing the reagents needed to perform Total CO2, Creatinine, and BUN assays, and considering the on-board inventory of the different reagent containers 30 as indicated, it is clear that one additional reagent container 30 for Total CO2 is needed for Tuesday and that two additional reagent containers 30 for Creatinine and BUN are needed for Tuesday. This information is displayed on display viewing screen 15S so that the requisite different reagent containers 30 may be timely supplied into tray 29 of analyzer and shuttled throughout analyzer 10 as required by a container transport system like seen in FIG. 6 in order to maintain a continuous throughput within analyzer 10.

TABLE 2

| Assays Per Reagent Container 30 | Assay Type | Averaged Assay Demand | Reagent Containers 30 on Analyzer 10 | Additional Reagent Containers 30 Needed on Analyzer 10 |
| --- | --- | --- | --- | --- |
| 540 | Total CO2 | 1255 | 2 | 1 |
| 450 | Creatinine | 1140 | 1 | 2 |
| 480 | BUN | 1050 | 1 | 2 |

As known in the art, an analyzer like analyzer 10 is not limited to the three assays in Table 1, and instead is typically adapted to perform as many as 180-200 different assays, with the reagents required to perform about 50% of these "on-board assays" always on-board analyzer 10 in storage areas 26, 27 and 28. In an exemplary embodiment of analyzer 10, in order to improve assay throughput, the reagent containers 30 containing reagents required to perform all "on-board assays" would be held in storage area 26 while the reagent containers 30 containing reagents required to perform less frequently requested all "on-board assays" might be divided between storage areas 27 and 28. When operated in this manner, about 250-500 assays per hour may be scheduled by computer 15 using reagent containers 30 held in storage area 26, while about 500 assays per hour may be scheduled by computer 15 using reagent containers 30 held in each of storage areas 27 and 28, so that computer 15 is scheduling between 1,250 to 1,500 assays per hour. These assay throughput values do not include about 375 ionic analyte measurements for sodium, potassium and chloride additionally performed by ion selective electron measuring station 47 on about 125 different samples per hour in aliquot vessel wells 52V.

Throughput values like those just described may be achieved because during operation of analyzer 10 by computer 15, different incoming samples 40 for which different assays are to be performed are partitioned into a number of separate assay groups in accord with the length of time required for the assay to be completed on reaction carousel 14, disclosed in co-pending application Ser. No. 10/151,424 (DCS-9128) and assigned to the assignee of the present invention. Judicious partitioning of assays by time, taken with carefully designed dwell times, number of reaction vessels 24, and location of assay devices 13 enables a first medium time length assay and a second shorter time length assay to be completed in less than a single operational cycle, thereby increasing the analyzer's 10 volume throughput as compared to conventional analyzers in which a reaction mixture having been analyzed may remain on a reaction carousel for an unproductive time period of inactivity. In particular, during a single full operational cycle of reaction carousel 14, medium length time assays are first completed within a number of reaction vessels 24; as each medium length time assay is completed, those reaction vessels 24 are removed from reaction carousel 14 and are replaced by new or cleaned reaction vessels 24 in which shorter length time assays are then completed. Longer length time assays remain on reaction carousel 14 during a full operational cycle.

Figure 9:
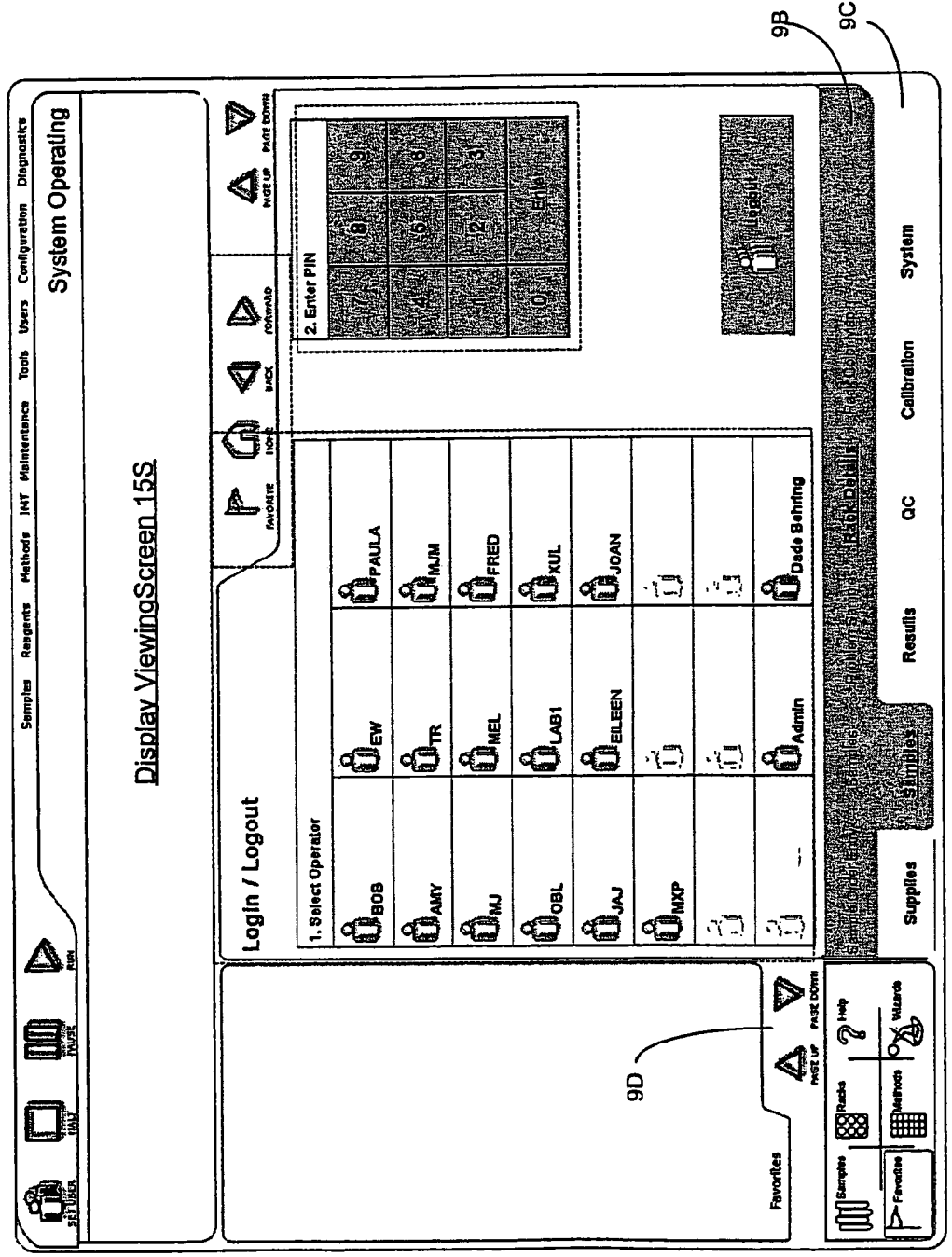
FIG. 9 is a viewing screen useful within the present invention.

Clearly, from the above descriptions of the multiple operations conducted within analyzer 10 as controlled by computer 15, it is apparent that a complex problem to be resolved is how to display to a clinical laboratory operator or to an analyzer technician on a display viewing screen 15S like illustrated in FIG. 9, that information pertinent to a given situation, in a "user-friendly" manner.

The display viewing screen 15S of a display module is segmented so that a significant portion, and preferably, a majority of the viewing screen 15S displays routine operational information that is used in routine operation of analyzer 10. Typically at least 90% of the viewing screen 15S displays routine operational information that is used in routine operation of analyzer 10. Routine operational information includes, for example, information about entering a sample order, checking on the status of a sample being analyzed, reading sample results, reading a list of the reagent containers 30 and calibration/Quality Control vial containers 30A needed to be loaded into tray 29 the next day, and the like. In contrast, less than 10% of the display viewing screen 15S displays non-routine or advanced operational information that is used in a detailed examination of information concerning the operation of analyzer 10. Advanced operational information includes, for example, information about which reagent container 30 lot is being used to currently perform each of the different assays analyzer 10 is equipped to perform, the expiration dates of each of the reagent lots, the calibration status of each of the reagent lots, a relative comparison of calibration coefficients between a new and a previous calibration, what are the existing calibration acceptance criteria, and the like.

FIG. 9 is a specific example of display viewing screen 15S in which the routine operational information occupies the lower, greater than 90% of screen 15S, identified as 9R and this information is easily accessed using only the tab rows 9B and 9C at the bottom of screen 15S and the Back/Forward buttons 9D. FIG. 9 illustrates how computer 15 is programmed to structure screen 15S on an operator specific basis so that a routine user cannot stumble into complexity that they are unable to handle. This structuring has implications in documentation and training programs, and also makes it much easier to train an operator to accomplish the essential functions required to maintain continuous throughput in analyzer 10, without needing to provide extensive overall operational knowledge. In contrast, older systems have been structured "by function", in which for example, all the complexity of calibration, is displayed in the same screen space. The routine operator was faced with the same functions available to the highly qualified and trained operator but did not have the training to address those issues. The routine screens used by computer 15 do not require a routine operator to even be aware of the complex, non-routine operational aspects of maintaining throughput of analyzer 10. If a problem arises, an alert is displayed, and the routine operator is taken where they need to go to resolve the issue, and the tools to accomplish it are close at hand. The routine screens display simple information and it is very difficult, if not impossible, to make an error, like destroy the store's inventory by pushing the wrong button. There is an advanced mode interface, which is available to highly trained and qualified technicians knowledgeable in the all of the non-routine aspects of a clinical chemistry system.

From the above description of analyzer 10, computer 15 is required to be programmed to control, among other items:
  analytical modules 17A, 17B, 17C, 17D;
  determine whether a reagent container 30 is new and unused;
  to conduct well-know calibration and quality control procedures as needed;
  incoming and outgoing sample tube transport system 36;
  patient's identity, the tests to be performed, if a sample aliquot is to be retained within analyzer 10;
  control and track the location of sample tubes 40, sample tube racks 42, and aliquot vessel arrays 52;
  operation of sampling probe 44;
  inventory and accessibility of sample aliquots within environmental chamber 38;
  ion selective electron probe 49 and ion selective electron measuring station 17D;
  aliquot vessel array transport system 50;
  reagent aspiration and dispense arms 60, 61 and 62 including liquid reagent probes 60P, 61P and 62P;
  reaction cuvette load station 61 and reaction vessel load station 63;
  wash station 67;
  linear container shuttle 72, reagent carousels 26A and 26B, shuttles 27S and 28S, reagent container trays 27T and 28T;
  tracking reagent and assay chemical solution consumption along with time, and date of consumption of all reagents consumed out of each reagent container 30 and assay chemical solutions consumed out of each vial container 30A on a per reagent container, per calibration vial container, per Quality Control container, per assay, and per calibration basis, for specifically defined time periods; and,
  scheduling between 1,250 to 1,500 assays per hour.

Figure 11:
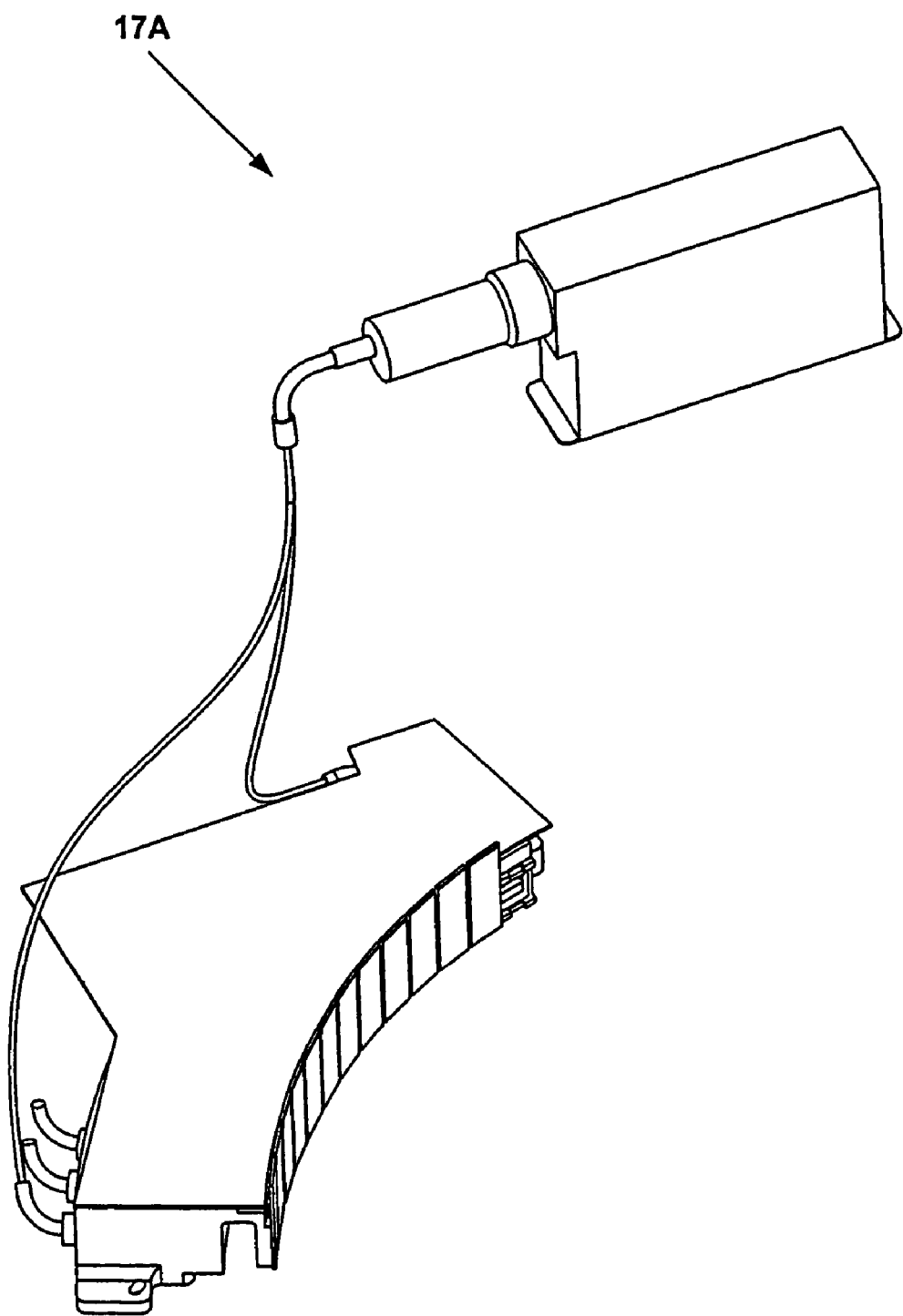
FIG. 11 is a perspective view of a photometric measuring device useful within the present invention; and, FIG. 12 is a perspective view of a LOCI measuring device useful within the present invention.

The above capabilities make possible the operation of analyzer 10 having a photometer analyzer or a turbidometer analyzer 17A and/or a nephelometer analyzer 17B like seen in FIG. 11 and a conventional luminometer analyzer or chemiluminometer analyzer 17C like seen in FIG. 12 and an ion selective electrode measuring station 17D like seen in FIG. 17D, thereby allowing for various diagnostic assays to be performed on a single analyzing system having higher sensitivity as well as faster processing speeds.

Those skilled in the art will readily appreciate that other conventional detectors may be selected for the detection units 17A, 17B, 17C and 17D, and that the relative positioning of the detection units 17A, 17B, 17C and 17D may be altered without departing from the scope of the invention. In the embodiment shown, the detection unit 17D utilized as an ion-selective electrode is positioned near the aliquot vessel array 52 from which it samples via a probe 49. However, in alternate embodiments, the detection unit 17D may be placed at other locations on the analyzer.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. An automated analyzer comprising:
   a rotatable reaction carousel supporting an outer cuvette carousel having cuvette ports formed therein and an inner cuvette carousel having vessel ports formed therein;
   a reaction cuvette load station positioned proximate said reaction carousel and containing a plurality of reaction cuvettes therein, said cuvette load station having means for placing said reaction cuvettes into said cuvette ports;
   a reaction vessel load station positioned proximate said reaction carousel and containing a plurality of reaction vessels therein, said vessel load station having means for placing said reaction vessels into said vessel ports;
   a luminescent oxygen channeling immunoassay reader surrounded by a light-shielding environmental chamber positioned proximate said reaction carousel and having means for detecting luminescence from a LOCI immunoassay reaction mixture in at least one of said reaction vessels;
   a detector comprising a photometer or a turbidometer or a nephelometer positioned proximate said reaction carousel and having means for performing analysis of a reaction mixture in at least one reaction cuvette;
   wherein said inner cuvette carousel comprises means for moving said reaction vessels to said luminescent oxygen channeling immunoassay reader and said outer cuvette carousel comprises means for moving said reaction cuvettes to said detector; and,
   a control mechanism having means for controlling said first and second detectors and said rotatable reaction carousel.

2. The automated analyzer of claim 1 wherein said LOCI immunoassay reaction mixture comprises a sensitizer capable of generating singlet oxygen upon absorbance of light.

3. The automated analyzer of claim 2 wherein said LOCI immunoassay reaction mixture further comprises a chemiluminescer capable of emitting light upon reaction with singlet oxygen.

* * * * *